United States Patent [19]

Schulz

[11] 4,147,250

[45] Apr. 3, 1979

[54] STORAGE AND INDEXING MECHANISM FOR MULTIPLE SAMPLE CONTAINERS

[75] Inventor: Isidore Schulz, Clarendon Hills, Ill.

[73] Assignee: Packard Instrument Company, Inc., Downers Grove, Ill.

[21] Appl. No.: 781,203

[22] Filed: Mar. 25, 1977

[51] Int. Cl.$^2$ .......................................... B65G 37/00
[52] U.S. Cl. .................................. 198/472; 198/861; 250/328; 108/26
[58] Field of Search ............... 198/339, 341, 345, 472, 198/580, 795, 860, 861; 250/328; 73/421 R, 423 A; 214/300, 301, 309, 310, 16.1 CC, 16.1 CD; 108/26, 20–22; 269/57; 23/230 R, 330.3, 253 R, 259

[56] References Cited

U.S. PATENT DOCUMENTS

| | | | |
|---|---|---|---|
| 958,475 | 5/1910 | Cannon | 108/22 |
| 1,660,743 | 2/1928 | Carroll | 108/26 |
| 3,257,561 | 6/1966 | Packard et al. | 250/328 |
| 3,270,202 | 8/1966 | Long et al. | 250/328 |
| 3,315,778 | 4/1967 | Kendall et al. | 198/472 |
| 4,001,585 | 1/1977 | Coutarel | 214/310 |
| 4,029,961 | 6/1977 | Lohr et al. | 250/328 |

Primary Examiner—Joseph E. Valenza

Attorney, Agent, or Firm—Leydig, Voit, Osann, Mayer & Holt

[57] ABSTRACT

A storage and indexing mechanism for a plurality of sample containers includes a portable tray for supporting and guiding the sample containers along preselected indexing paths on the tray. The sample containers can be pre-loaded on the tray with the tray being used for storage and transport of the sample containers. When it is desired to process the sample containers, as in a scintillator counter or other analytical instrument, the portable tray containing the sample containers is placed on a stationary stage for receiving and holding the tray on the analytical instruments. The stage includes means cooperating with the tray for indexing the sample containers along the indexing paths on the tray when the tray is mounted on the stage, and means for registering the tray and the sample containers thereon with the indexing means when the tray is mounted on the stage. Latching means are provided for releasably latching the tray to the stage in register with the indexing means, and locking means are provided for locking the sample containers against sliding movement on the tray when the tray is removed from the stage. The locking means is responsive to the release of the latching means for automatically locking the sample containers whenever the tray is released from the stage by the latching means.

4 Claims, 11 Drawing Figures

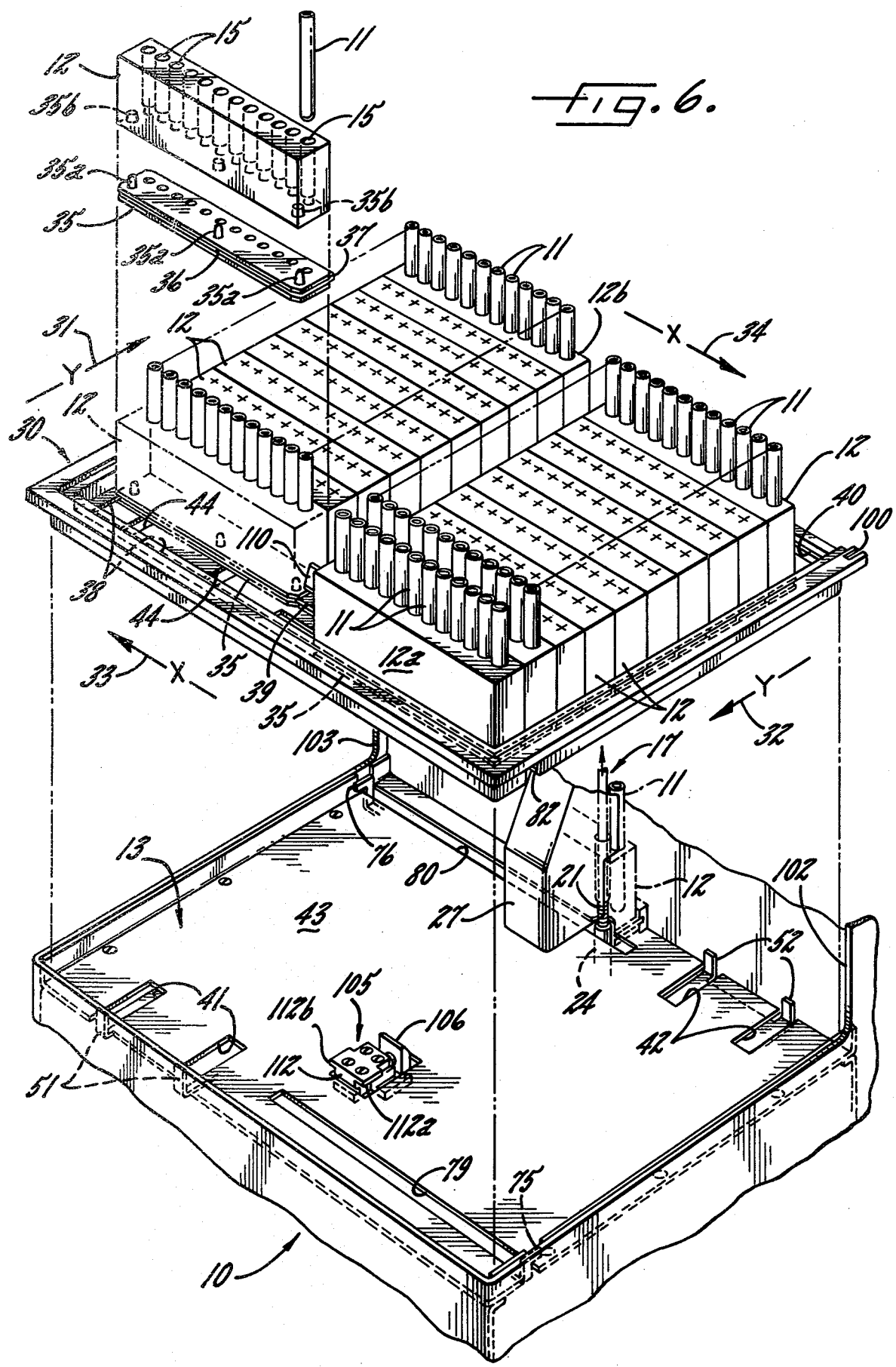

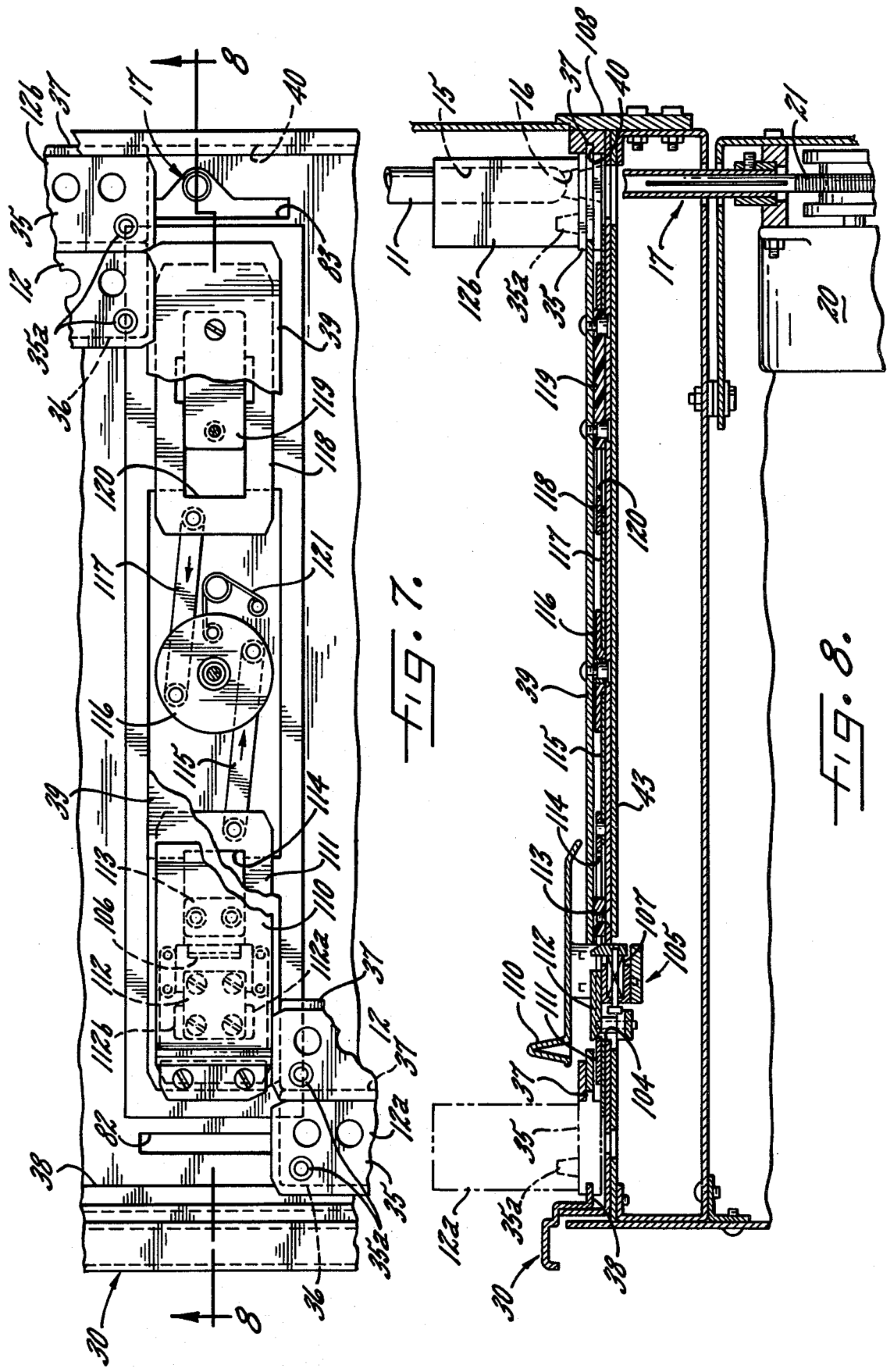

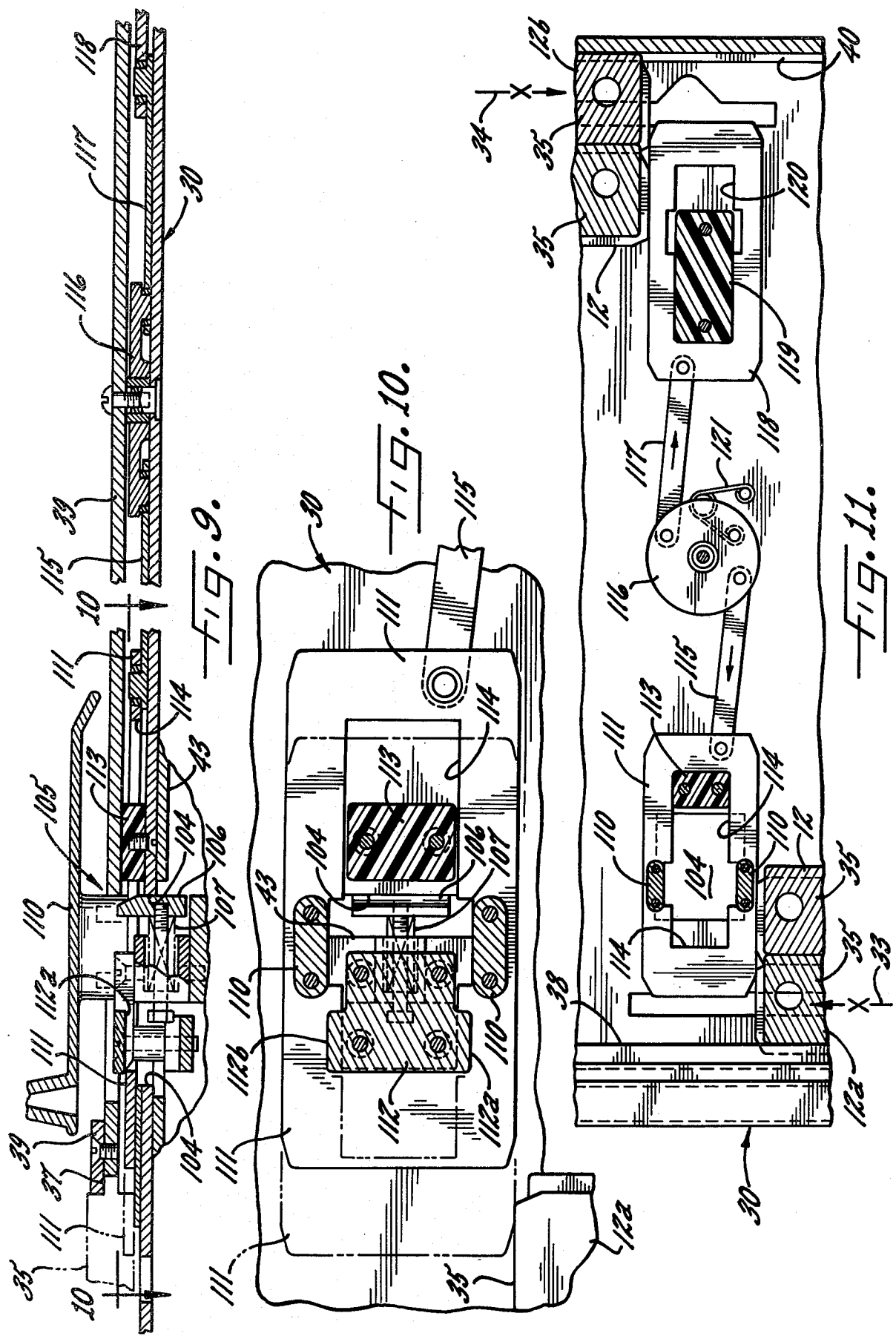

STORAGE AND INDEXING MECHANISM FOR MULTIPLE SAMPLE CONTAINERS

DESCRIPTION OF THE INVENTION

The present invention relates generally to article storage and indexing systems and, more particularly, to x-y indexing systems that are also capable of storing a multiplicity of the articles being indexed.

It is a principal object of the present invention to provide an improved storage and indexing mechanism which facilitates the handling of relatively large groups of articles such as laboratory samples. Thus, one specific object of the invention is to provide such a mechanism that permits the entire capacity of an analytical laboratory instrument, such as a scintillation counter with an automatic sample changer, to be handled as a single unit.

Another important object of the invention is to provide an improved storage and indexing mechanism of the foregoing type that is compatible with automatic sample changing mechanisms, so that the entire system can be left unattended for automatic operation until all the samples or other articles have been processed.

It is a further object of the invention to provide such an improved storage and indexing mechanism which securely holds the articles therein during handling of the mechanism as well as during indexing movements thereof.

Yet another object of the invention is to provide such an improved storage and indexing mechanism which has a high degree of reliability in operation, and is simple to operate.

Other objects and advantages of the invention will be apparent from the following detailed description and the accompanying drawings, in which:

FIG. 6 is an enlarged exploded perspective of the storage and indexing mechanism in the instrument of FIGS. 1-5, loaded with a multiplicity of laboratory samples;

FIG. 7 is an enlarged top plan view of the latching assembly in the center of the storage and indexing mechanism of FIGS. 1-6;

FIG. 8 is a vertical section taken substantially along line 8—8 of FIG. 7;

FIG. 9 is an enlarged view of the forward portion of the latching assembly shown in the sectional view of FIG. 8;

FIG. 10 is a horizontal section taken substantially along line 10—10 in FIG. 9; and FIG. 11 is a plan view of a portion of the latching mechanism shown in FIG. 7 but in its advanced or latched position.

While the invention will be described in connection with certain preferred embodiments, it is to be understood that the invention is not limited to these particular embodiments. On the contrary, it is intended to cover all alternatives, modifications and equivalent arrangements as may be included within the spirit and scope of the invention as expressed in the appended claims.

Figures 1, 2:
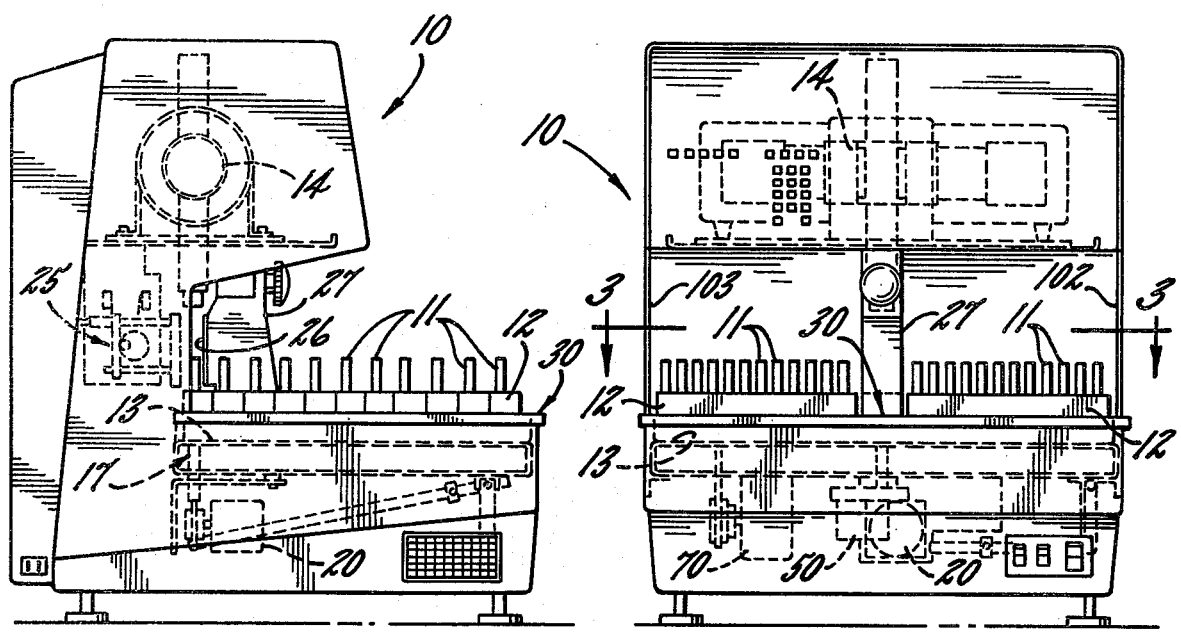
FIG. 1 is a side elevation of a bench top scintillation counter including a storage and indexing mechanism embodying the present invention.
FIG. 2 is a front elevation of the scintillation counter of FIG. 1.

Turning now to the drawings and referring first to FIGS. 1 and 2, there is shown a bench top scintillation counter 10, in which the present invention finds one of its many applications. Rows of tubes 11 containing radioactive samples are shown resting in rows of cassettes 12 on a stage 13 of the counter, ready to be advanced in seriatim to a transfer station where they are elevated into a counting chamber 14. Each of the cassettes 12 holds a multiplicity of sample tubes 11, with each of the tubes resting loosely in a compartment 15 in the cassette. These tubes 11 may be of different heights and diameters if desired. Apertures 16 in the cassettes 12 below each compartment 15 are of smaller transverse dimension than the smallest tube in order to support the tubes within the cassette 12, and yet these apertures 16 are large enough to allow an elevator pedestal 17 to pass therethrough at the transfer station.

When one of the apertures 16 in a cassette 12 is aligned with the transfer station, directly over the elevator pedestal 17, advancing movement of the elevator pedestal 17 through the aperture 16 raises one of the tubes 11 into the overhead chamber 14 for counting. Vertical movement of the elevator pedestal 17 is controlled by a drive motor 20 which raises and lowers an elongated tightly coiled spring 21 attached to the lower end of the pedestal 17. The trailing end of the coiled spring 21 is telescoped within a stationary hollow tube 24 beneath the stage 13, the tube 24 being bent to fit within the available space beneath the stage 13.

For the purpose of guiding the elevator pedestal 17 and the tube 11 carried thereby during vertical movement to and from the counting chamber 14, a retractable guide assembly 25 is mounted adjacent the rear side of the transfer station. This retractable guide assembly cooperates with a stationary guide plate 26 secured to the back of a thermal printer 27 adjacent the front side of the transfer station. The purpose of the thermal printer 27 is to automatically print the sample count onto a record strip carried on the side of each cassette 12, which is not part of the present invention.

Figure 3:
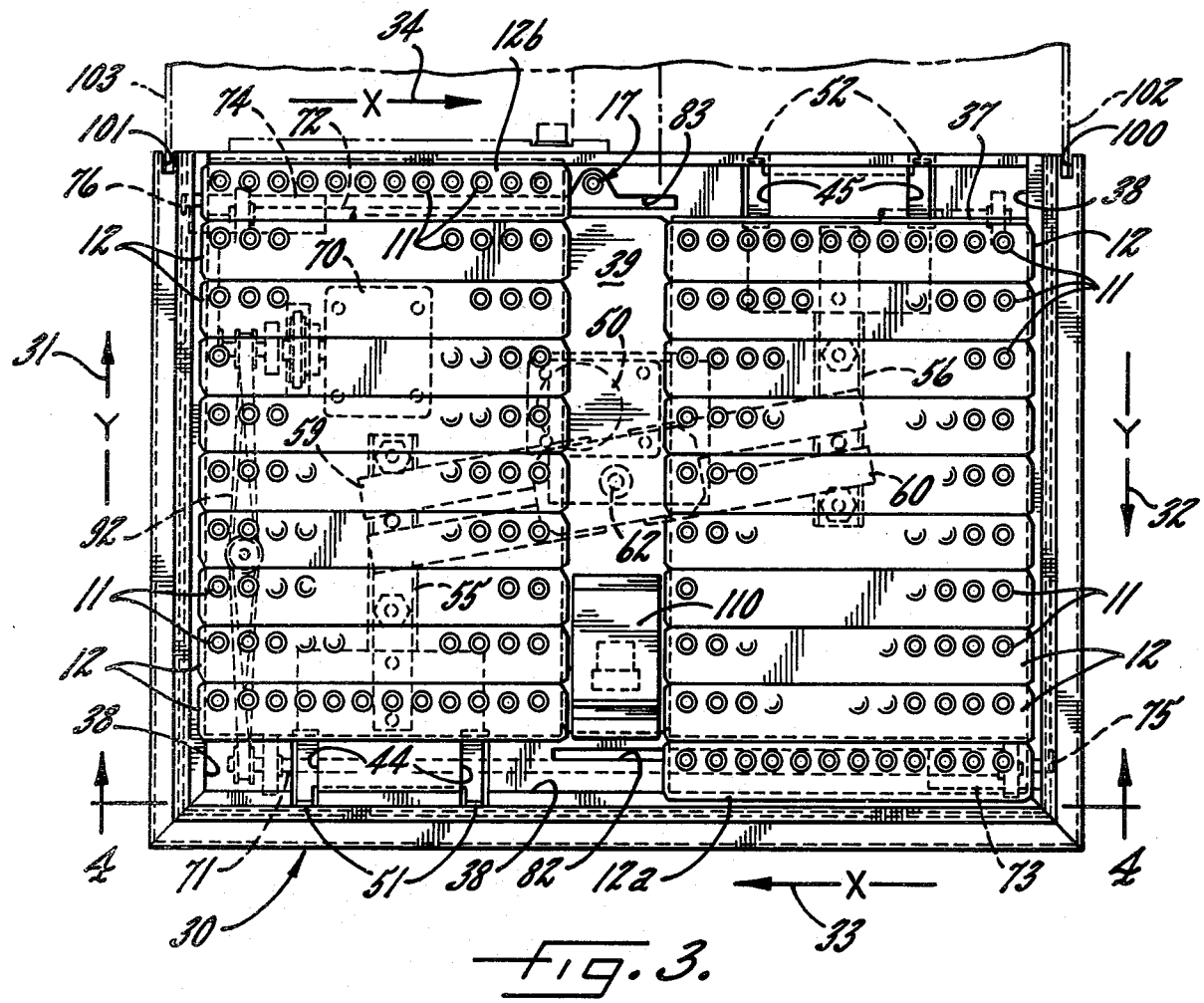
FIG. 3 is an enlarged partial section taken substantially along line 3—3 in FIG. 2.

In accordance with one important aspect of the present invention, the plurality of cassettes 12 are supported and guided along preselected indexing paths on a portable tray adapted to be mounted on the stationary stage in cooperation with means for indexing the cassettes along the indexing paths on the tray, and means are provided for automatically registering the tray and the cassettes thereon with the indexing means when the tray is mounted on the stage. Thus, in the illustrative embodiment, two rows of ten cassettes each are mounted on a tray 30 for indexing movement along two y-direction paths 31 and 32 and two x-direction paths 33 and 34. As can be seen most clearly in FIGS. 3 and 6, the two y-direction paths 31 and 32 extend parallel to the sides of the tray 30, perpendicular to row of sample tubes 11 in each cassette 12, while the two x-direction paths 33 and 34 extend along the front and rear of the tray, parallel to the row of sample tubes 11 in each cassette. The x and y paths thus form a closed loop extending around the perimeter of the tray, with the rear x path 34 crossing the elevator pedestal 17 at the vertical transfer station.

For the purpose of guiding the cassettes 12 along the desired indexing paths on the tray 30, the tray carries a plurality of base plates 35 each of which is coextensive with the bottom surface of one of the cassettes 12. Each base plate 35 includes a series of raised pins 35a which mesh with complementary sockets 35b in the bottoms of the cassettes 12 to hold the cassettes in place on the base plates. The base plates 35 and the tray 30 form a series of cooperating tongues and grooves which guide the base plates 35, and thus the cassettes 12 carried thereby, along the x and y indexing paths 31–34. More specifically, each of the base plates 35 includes a groove 36 extending along the front and both ends of the base plate, and a tongue 37 on the rear of the base plate. These tongues 37 and grooves 36 mesh with adjacent base plates 35 and also with (1) a tongue 38 formed by an inturned flange extending along the front and both side walls of the tray 30, (2) the edges of a central guide plate 39 formed as a part of the tray, and (3) a groove 40 in the rear wall of the tray 30. Thus, as can be seen most clearly in FIG. 6, the base plates 35 are always supported by this tongue-and-groove structure on at least three of the four edges of each base plate as they are indexed around the closed loop formed by the x and y paths 31–34.

To permit indexing movement of the cassettes 12 and their base plates 35 along the two x paths 33 and 34, there is never more than one cassette 12 and base plate 35 in either one of these paths. For example, in the arrangement illustrated in FIG. 6, the front x path 33 contains only one cassette 12a ready to be indexed from right to left along the front of the tray 30, and the rear x path 34 contains only one cassette 12b ready to be indexed from left to right along the rear of the tray 30, bringing successive tubes 11 into register with the elevator pedestal 17. Each time the indexing movement of two cassettes, e.g. the cassettes 12a and 12b, is completed along the length of the respective x paths 33 and 34, the two rows of cassettes are then indexed one step in the y direction to bring a new pair of cassettes into alignment with the x paths 33 and 34. That is, the cassettes in the y path 31 are indexed toward the rear of the tray, and the cassettes in the y path 32 are indexed toward the front of the tray.

In the particular embodiment illustrated, the maximum number of cassettes that can be accommodated by the tray 30 is 20 cassettes. Any lesser number of cassettes may be mounted on the tray at any given time, but the tray always contains 20 base plates 35 because, as will be apparent from the ensuing description, the base plates 35 are an essential part of the y indexing mechanism because they push each other along the y paths 31 and 32. That is, the drive mechanism associated with the y paths 31 and 32 is designed to advance the base plates 35 through a distance corresponding to only one base plate width, relying on each base plate 35 to push the next adjacent plate to move the entire row of plates in the y direction.

For the purpose of indexing the cassettes 12 and their base plates 35 in the y direction, a reversible drive motor 50 mounted on a chassis base plate 46 reciprocates a first pair of lugs 51 at the front of the y path 31 and a second pair of lugs 52 at the rear of the y path 32. These lugs 51 and 52 project upwardly through corresponding slots 41 and 42 formed in a chassis cover plate 43 that supports the tray 30 when it is inserted into the counter 10, and through corresponding slots 44 and 45 in the tray itself. The coupling between the drive motor 50 and the two pairs of lugs 51 and 52 is illustrated most clearly in FIGS. 4–6, where it can be seen that the lugs 51 and 52 are formed as integral parts of a pair of plates 53 and 54, respectively, carried by a pair of ball bearing slide assemblies 55 and 56 mounted on the base plate 46. These slide assemblies 55 and 56 carry a pair of vertical pins 57 and 58 which ride in slots formed by a pair of transfer arms 59 and 60, respectively, for the purpose of converting rotational movement of the transfer arms 59 and 60 into linear reciprocating movement of the slide assemblies 55 and 56. The transfer arms 59 and 60 are fastened to a bracket 61 mounted on the shaft 62 of the drive motor 50.

Thus, when the drive motor 50 is energized, it rotates the bracket 61 and the transfer arms 59 and 60, thereby reciprocating the pins 57 and 58 and their corresponding slide assemblies 55 and 56 back and forth along the respective y paths 31 and 32. This reciprocating movement of the slide assemblies 55 and 56 repetitively advances and retracts the two pairs of lugs 51 and 52, thereby indexing the base plates 35 and cassettes 12 along the two y paths 31 and 32. More specifically, the front lugs 51 index the left-hand row of cassettes 12 (as viewed in FIG. 6) rearwardly over the tray 30 along the path 31, while the rear lugs 52 index the right-hand row of cassettes forwardly over the tray along the path 32. As can be seen in FIG. 6, the distance traversed by the lugs 51 and 52 is only the y-direction width of one of the base plates 35, but the particular base plates engaged by the lugs push the other base plates and their cassettes along the respective y paths so that the entire row of cassettes is indexed in response to each advancing movement of the lugs 51 and 52.

Figure 4:
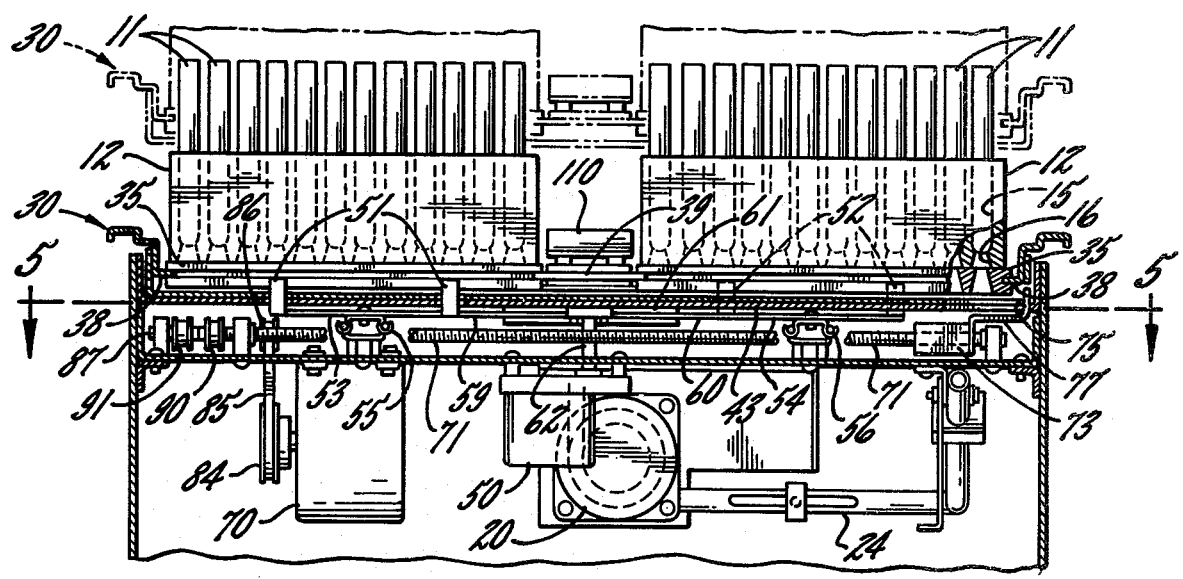
FIG. 4 is a vertical section taken substantially along line 4—4 in FIG. 3.
Figure 5:
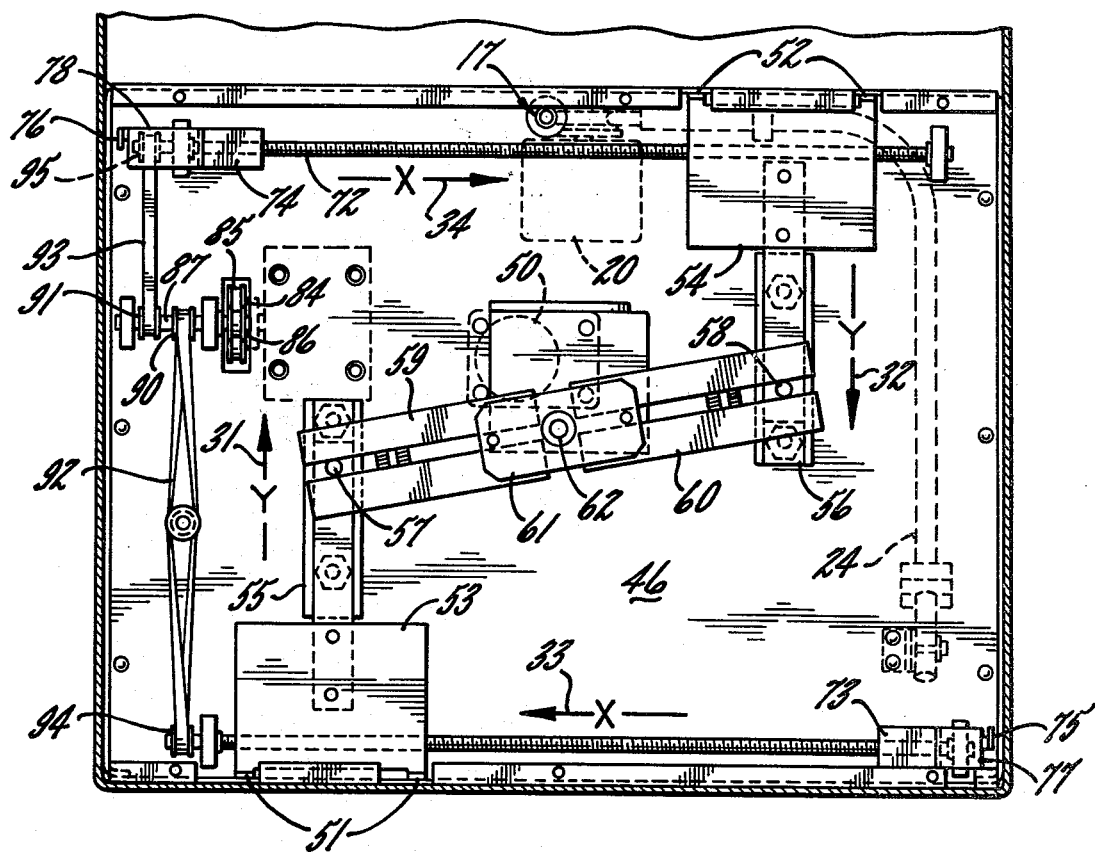
FIG. 5 is a horizontal section taken substantially along line 5—5 in FIG. 4.

The drive system for indexing the cassettes 12 and their base plates 55 along the x paths 33 and 34 is also shown most clearly in FIGS. 4–6. Thus, a drive motor 70 mounted on the base plate 46 rotates a pair of threaded shafts 71 and 72 journaled on the base plate 46 in alignment with the two x paths 33 and 34. Mounted on these two shafts 71 and 72 are a pair of internally threaded traverse blocks 73 and 74 which move back and forth along the respective threaded shafts 71 and 72 in response to rotation of the shafts. During this reciprocating movement of the traverse blocks 73 and 74, they carry with them a pair of upstanding lugs 75 and 76 which are mounted on the corresponding blocks by brackets 77 and 78.

To enable the lugs 75 and 76 to engage the ends of the two base plates 35 aligned with the two x paths 33 and 34 at any given time, the lugs 75 and 76 extend upwardly through a pair of elongated slots 79 and 80, formed in the cover plate 43, and through corresponding slots 82 and 83 formed in the bottom wall of the tray 30. During advancing movement of the lugs 75 and 76, the front cassette 12a is indexed from right to left along the x path 33 at the front of the tray 30 (as viewed in FIG. 6), and the rear cassette 12b is indexed from left to right along the x path 34 at the rear of the tray. Indexing movement of the rear cassette 12b along the path 34 places successive tube apertures 16 in register with the elevator pedestal 17 so that successive sample tubes 11 can be raised into the counting chamber 14 and then returned to the cassette 12. Thus, the advancing indexing movement in the x direction is effected in twelve steps with a dwell interval between successive steps to allow time for each sample tube 11 to be elevated into the counting chamber 14 and then returned to its cassette. This stepwise advancing movement may be effected by turning the motor 70 on and off at fixed time intervals, or the motor may be controlled by sensing elements responsive to the movement of the cassette 12b and the return of the sample tubes 11 thereto.

Although the x-direction drive motor 70 may be coupled to the threaded shafts 71 and 72 in a variety of different ways, the particular embodiment illustrated has a pulley 84 mounted on the drive shaft of the motor 70 and carrying a drive belt 85 for turning a pulley 86 on a shaft 87. The shaft 87 carries a pair of pulleys 90 and 91 which drive respective belts 92 and 93 connected to corresponding pulleys 94 and 95 on the threaded shafts 71 and 72. The shafts 71, 72 and 87 are all journalled in fixed bearing blocks secured to the chassis base plate 46.

When the tray 30 is first placed on the stage 13, it is aligned in the transverse direction by fitting a pair of slots 100 and 101 in the rear corners of the tray over a pair of forwardly projecting flanges 102 and 103 on the side walls of the instrument at the rear of the stage. The front portion of the tray is then lowered to bring an aperture 104 in the front central portion of the tray bottom into register with a tray latch assembly 105 mounted on the cover plate 43 and projecting upwardly therefrom. As the tray is lowered over the latch 105, the rear edge of the aperture 104 engages a beveled surface on a spring-loaded biasing plate 106 projecting above the chassis cover plate 43. Continued downward movement of the tray against the beveled surface of the biasing plate 106 retracts the plate 106 against the urging of a biasing spring 107, with the spring 107 urging the tray firmly against a rear wall 108 of the chassis.

In accordance with another important aspect of the invention, a latching mechanism is provided for releasably latching the tray in a predetermined position on the stage, and for releasably locking the cassette base plates 35 against sliding movement across the tray when the tray is removed from the stage. In the illustrative embodiment, this latching mechanism is illustrated in FIGS. 6-11.

After the tray 30 has been lowered over the latch assembly 105 onto the chassis cover plate 43, a latch handle 110 projecting upwardly through an elongated aperture in the center guide plate 39 of the tray is moved toward the rear of the tray so as to slide a latch plate 111 beneath a pair of laterally projecting ears 112a, 112b on a latch block 112. The latch plate 111 is fastened to the bottom of the handle 110 and is held captive between the bottom wall of the tray and the center guide plate 39, being guided by a stationary spacer block 113 mounted on the bottom wall 43 within a central elongated aperture 114 in the latch plate 111. Consequently, the capture of this plate 111 beneath the ears 112a, 112b firmly latches the tray 30 to the chassis cover plate 43 on which the latch block 112 is mounted. When it is desired to remove the tray from the chassis, the latch handle 110 is simply moved toward the front of the tray, thereby bringing the aperture 114 in the latch plate 111 into register with the tray latch assembly 105 so that the tray will clear the latch assembly 105 when lifted off the cover plate 43.

When the latch plate 111 is moved toward the front of the tray 30 to unlatch the tray from the chassis, the front of the latch plate 111 also locks the cassette base plate 35 at the very front of the tray against sliding movement in the x direction. As will be described in more detail below, a similar lock is effected at the rear of the tray to prevent sliding movement of the rearmost base plate 35 in the x direction, so that all the cassette base plates are locked against transverse sliding movement on the tray while the tray is removed from the chassis cover plate 43 and transported to a different location. Thus, when the forward latch plate 111 is moved toward the front of the tray, against the spacer block 113, it projects beyond the front edge of the center guide plate 39 and into the x path 33 to block movement of the front base plate 35 along the path 33. At the same time, the forward movement of the latch plate 111 advances a lever 115 to rotate a bell crank 116 and thereby advance a second lever 117 to slide a rear latch plate 118 toward the rear of the tray. This moves the rear latch plate 118 into locking engagement with the rearmost cassette base plate 35 at the rear of the tray to block movement of the base plate along the x path 34 thereby locking all the base plates and the cassettes 12 thereon against sliding movement in the x direction. Advancing movement and retracting movement of the rear latch plate 118 is guided and limited by a spacer block 119 mounted on the tray bottom wall within an elongated aperture 120 in the plate 118.

To facilitate movement of the latch plates 111 and 118 in response to manual pressure on the latch handle 110 in either direction, a bell crank spring 121 is connected to the bell crank 116. When the latch plates 111 and 118 are in their retracted positions, the spring 121 is in the position illustrated in FIG. 7, biasing the bell crank in the counterclockwise direction which urges the latch plates toward their attracted positions. When the latch plates 111 and 118 are in their advanced positions, the spring 121 is in the position illustrated in ,IG. 11, biasing the latch plates toward their advanced positions. Thus, it can be seen that the spring 121 assists the movement of the bell crank in both directions in response to manual operation of the latch handle 110.

I claim as my invention:

1. A storage and indexing mechanism for a plurality of sample containers, said mechanism comprising the combination of
   (a) a portable tray for supporting and guiding a plurality of said sample containers along preselected indexing paths on the tray,
   (b) a stationary stage for receiving and holding said tray and including
      (1) means for indexing said sample containers along said indexing paths on said tray when the tray is mounted on said stage, and
      (2) means for automatically registering said tray and the sample containers thereon with said indexing means when said tray is mounted on said stage, and means for locking said sample containers against sliding movement on said tray when the tray is removed from said stage.

2. A storage and indexing mechanism as set forth in claim 1 which includes means for releasably latching said tray to said stage in register with said indexing means, and said locking means is responsive to the release of said latching means for automatically locking the sample containers whenever the tray is released from the stage.

3. A storage and indexing mechanism for a plurality of sample containers, said mechanism comprising the combination of
   (a) a portable tray for supporting and guiding a plurality of said sample containers along preselected indexing paths on the tray,
   (b) a stationary indexing stage for receiving and holding said tray and including:
      (1) means for releasably latching said tray in a predetermined position on said stage, (2) means for indexing successive groups of said sample containers in the y direction on said tray so as to bring successive containers into register with an x-direction indexing station,
(3) and means for indexing individual sample containers in the x direction on said tray at said indexing station, and means for locking said sample containers against sliding movement on said tray in the x direction when the tray is removed from said stage.

4. A storage and indexing mechanism as set forth in claim 3 wherein said locking means is responsive to the release of said latching means for automatically locking the sample containers whenever the tray is released from the stage.

* * * * *